(12) United States Patent
Lee et al.

(10) Patent No.: US 10,392,344 B2
(45) Date of Patent: Aug. 27, 2019

(54) METHOD FOR PREPARING FLUORINE-18 ELUENT WITH ADJUSTED PH, AND METHOD FOR LABELLING FLUORINE-18 USING SAME

(71) Applicant: THE ASAN FOUNDATION, Seoul (KR)

(72) Inventors: Sang Ju Lee, Seoul (KR); Seung Jun Oh, Seoul (KR); Dae Hyuk Moon, Seoul (KR); Jin Sook Ryu, Seoul (KR); Jae Seung Kim, Seoul (KR); Jong Jin Lee, Seoul (KR)

(73) Assignee: THE ASAN FOUNDATION, Seoul (KR)

( * ) Notice: Subject to any disclaimer, the term of this patent is extended or adjusted under 35 U.S.C. 154(b) by 180 days.

(21) Appl. No.: 14/375,412

(22) PCT Filed: Dec. 21, 2012

(86) PCT No.: PCT/KR2012/011273
§ 371 (c)(1),
(2) Date: Jul. 29, 2014

(87) PCT Pub. No.: WO2013/115483
PCT Pub. Date: Aug. 8, 2013

(65) Prior Publication Data
US 2015/0045548 A1    Feb. 12, 2015

(30) Foreign Application Priority Data
Jan. 30, 2012  (KR) .................... 10-2012-0009009

(51) Int. Cl.
| | | |
|---|---|---|
| *C07C 303/32* | (2006.01) | |
| *C07B 59/00* | (2006.01) | |
| *C07C 217/80* | (2006.01) | |
| *C07C 309/01* | (2006.01) | |
| *C07D 213/64* | (2006.01) | |
| *C07D 233/91* | (2006.01) | |
| *C07D 451/02* | (2006.01) | |
| *C07H 19/06* | (2006.01) | |
| *C07D 403/06* | (2006.01) | |
| *C07C 213/08* | (2006.01) | |
| *C07D 471/04* | (2006.01) | |
| *C07C 253/30* | (2006.01) | |
| *A61K 51/04* | (2006.01) | |

(52) U.S. Cl.
CPC ............ *C07C 303/32* (2013.01); *A61K 51/04* (2013.01); *A61K 51/0455* (2013.01); *C07B 59/00* (2013.01); *C07C 213/08* (2013.01); *C07C 217/80* (2013.01); *C07C 253/30* (2013.01); *C07C 309/01* (2013.01); *C07D 213/64* (2013.01); *C07D 233/91* (2013.01); *C07D 403/06* (2013.01); *C07D 451/02* (2013.01); *C07D 471/04* (2013.01); *C07H 19/06* (2013.01); *C07B 2200/05* (2013.01)

(58) Field of Classification Search
CPC .... C07C 303/32; C07B 59/00; C07B 2200/05
USPC ........................................................ 424/1.89
See application file for complete search history.

(56) References Cited

U.S. PATENT DOCUMENTS

2014/0256970 A1* 9/2014 Jackson ........................... 552/1

FOREIGN PATENT DOCUMENTS

| WO | WO 2011127345 A1 * | 10/2011 | |
| WO | WO 2011151283 A1 * | 12/2011 | ............. A61K 51/04 |

OTHER PUBLICATIONS

Pohar et al. J. Sol. Chem. 1998, 27, 1033-1043.*
Kohno et al. Aust. J. Chem. 2011, 64, 1560-1567.*
Svadberg et al. J. Nucl. Med. 2011, 52, 465.*
Bonner et al. J. Am. Chem. Soc. 1981, 103, 3262-3265.*
Lang, L. et al. (1997) "Labeling Proteins at High Specific Activity using N-succinimidyl 4[$^{18}$F](fluoromethyl) Benzoate," Appl. Radial. Isto. 48(2):169-173.
Lee, S.J. et al. (2011) "New automated synthesis of [$^{18}$F]FP-CIT with base amount control affording high and stable radiochemical yield: a 1.5-year production report," Nuclear Medicine and Biology 38:593-597.
Moon, B.S. et al. (2010) "Highly efficient production of [$^{18}$F]fallypride using small amounts of base concentration," Applied Radiation and Isotopes 68:2279-2284.
Ohsaki, K. et al. (1998) "Polymer-supported Catalysts for Efficient On-column Preparation of 2-Deoxy-2-[$^{18}$F]fluoro-D-glucose," Applied Radiation and Isotopes 49(4):373-378.

(Continued)

Primary Examiner — Michael G. Hartley
Assistant Examiner — Sean R Donohue
(74) Attorney, Agent, or Firm — Foley & Lardner LLP; Antoinette F. Konski

(57) ABSTRACT

The present invention relates to a method for labelling fluorine-18, which is a radioisotope, and more specifically, to a method for labelling a [$^{18}$F]fluoride in a method for preparing an organic [$^{18}$F]fluoro compound by reacting an alkyl halide or an alkyl sulfonate with a [$^{18}$F]fluoride, wherein a [$^{18}$F]fluoride supported on a quaternary alkyl ammonium polymer support is eluted using a solution containing a metal salt or a quaternary ammonium salt with an adjusted pH, and a base is not additionally used. The present invention enables a labeling reaction without an additional base after precisely reflecting the concentration of a base absolutely necessary for the nucleophilic substitution of a [$^{18}$F]fluoride or eluting a [$^{18}$F]fluoride using a [$^{18}$F]fluoride eluent with an adjusted pH, thereby stably obtaining a [$^{18}$F]fluoride-labelled compound in a high yield, and is thus useful for production of fluorine-18-labelled radioactive medical supplies.

5 Claims, 3 Drawing Sheets

(56) References Cited

OTHER PUBLICATIONS

Seo, J.W. et al. (2011) "Fast and Easy Drying Method for the Preparation of Activated [$^{18}$F]Fluoride Using Polymer Cartridge," Bull. Korean Chem. Soc. 32(1):71-76.
Suehiro, M. et al. (2007) "Investigation of the role of the base in the synthesis of [$^{18}$F]FLT," Applied Radiation and Isotopes 65:1350-1358.
International Search Report (ISA/KR) for International Application No. PCT/KR2012/011273, dated Apr. 5, 2013, 2 pages.

* cited by examiner

METHOD FOR PREPARING FLUORINE-18 ELUENT WITH ADJUSTED PH, AND METHOD FOR LABELLING FLUORINE-18 USING SAME

CROSS-REFERENCE TO RELATED APPLICATIONS

This application is a national stage application under 35 U.S.C. § 371 of International Application No. PCT/KR2012/011273, filed Dec. 21, 2012, which in turn claims priority to Korean Application No. 10-2012-0009009 filed Jan. 30, 2012, the content of each of which is incorporated herein in its entirety by reference.

TECHNICAL FIELD

The present invention relates to a method for labeling with fluorine-18 which can accurately reflect the concentration of a base required for a reaction using an [$^{18}$F]fluoride eluent containing a metal salt or quaternary ammonium salt with an adjusted pH without the addition of a base.

BACKGROUND ART

With the development of modern civilization, the quality of life has been improved, and with the medical development, the human lifespan has increased. However, the occurrence of various diseases, such as brain diseases including Parkinson's disease, depression, schizophrenia, Alzheimer's disease, etc.; heart diseases due to stress and dietary change; and various cancers due to exposure of humans to toxic substances, is gradually increasing. Accordingly, there is a need to develop an imaging diagnostic method which can diagnose these diseases at an early stage.

While various imaging diagnostic methods have been commercialized, positron emission tomography (PET) can be readily applied to clinical practice. The positron emission tomography is used to image the distribution of radiopharmaceuticals in vivo and their biochemical changes by intravenously injecting an organic compound labeled with a positron-emitting radioisotope. Therefore, it is possible to quantitatively measure in vivo biochemical changes at a lesion site through the positron emission tomography, which makes it possible to measure the progression of disease and predict the degree of treatment [A. Agool, R. H. Slart, K. K. Thorp, A. W. Glaudemans, D. C. Cobben, L. B. Been, F. R. Burlage, P. H. Elsing a, R. A. Dierckx, E. Vellenga, J. L. Holter, *Nucl. Med. Commun.* 2011, 32, 14.; N. Aide, K. Kinross, C. Cullinane, P. Roselt, K. Waldeck. O, Neels, D. Dorow, G. McArthur, R. J. Hicks, *J. Nucl. Med.* 2011, 51, 1559.; A. Debucquoy, E. Devos, P. Vermaelen, W. Landuyt, S. De Weer, F. Van Den Heuvel, K. Haustermans, *Int. J. Radiat. Biol.* 2009, 85, 763].

Radioisotopes used in the positron emission tomography include fluoride ([$^{18}$F]F), carbon ([$^{15}$C]C), nitrogen ([$^{13}$N]N), oxygen ([$^{15}$O]O), gallium ([$^{68}$Ga]Ga), etc., and it is reported that the [$^{18}$F]fluoride is of similar size to hydrogen, forms a stable bond with a carbon atom of an organic compound, is easy to be produced, and has an appropriate half-life (110 minutes), and thus is very suitable for the positron emission tomography [Lasne, M. C.; Perrio, C.; Rouden, J.; Barre, L.; Roeda, D.; Dolle, F.; Crouzel, C. *Contrast Agents II, Topics in Current Chemistry*, Springer-Verlag, Berlin, 2002, 222, 201-258.; Bolton, R. J. *Labelled Compd. Radiopharm.* 2002, 45 485-528].

In general, an organofluoro-18 compound is produced by reacting an alkyl halide or alkyl sulfonate with a fluorine salt, followed by substitution of a fluoride, and the [$^{18}$F] fluoride is mainly used as the fluorine salt.

In the above alkyl halide or alkyl sulfonate, the halide is selected from the group consisting of Cl, Br, and I other than F, the sulfonate is —SO$_3$R$^{12}$, and R$^{12}$ is an alkyl group or aryl group. More specifically, the alkyl group is preferably a C$_1$-C$_{12}$ alkyl sulfonate or halo C$_1$-C$_{12}$ alkyl group, and examples thereof include methanesulfonate, ethanesulfonate, isopropanesulfonate, chloromethanesulfonate, trifluoromethanesulfonate, and chloroethanesulfonate. Moreover, the aryl group is preferably selected from the group consisting of a phenyl group, a C$_1$-C$_4$ alkyl phenyl group, a halo phenyl group, a C$_1$-C$_4$ alkoxy phenyl group, and a nitrophenyl group, and preferred examples thereof include methylphenylsulfonate, ethylphenylsulfonate, chlorophenylsulfonate, bromophenylsulfonate, methoxyphenylsulfonate, and nitrophenylsulfonyl.

In general, the [$^{18}$F]fluoride may be produced by irradiating [$^{18}$O]H$_2$O with protons using a cyclotron that is a circular accelerator [M. R. Kilbourn, J. T. Hood, M. J. Welch, *Int. J. Appl. Radiat. Isot.* 1984, 35, 599.; G. K. Mulholland, R. D. Hichwa, M. R. Kilbourn, J. Moskwa, *J. Label. Compd. Radiopharm.* 1989, 26, 140]. Moreover, the [$^{18}$F]fluoride is generally produced at a very low concentration in [$^{18}$O]H$_2$O solution, and the [$^{18}$O]H$_2$O solution is very expensive in terms of price and thus is recycled [K.-I, Nishijima, Y. Kuge, E. Tsukamoto, K.-I. Seki, K. Ohkura, Y. Magata, A. Tanaka, K. Nagatsu, N. Tamaki. *Appl. Radiat. Isot.* 2002, 57, 43; D. Schoeller, *Obes. Res.* 1999, 7, 519.; *SNM Newsline, J. Nucl. Med.* 1991, 32, 15N].

In order to remove a small amount of metal impurities produced during the recycling of the [$^{18}$O]H$_2$O solution and during the production of [$^{18}$F]fluoride and to use only the production of [$^{18}$F]fluoride in a labeling reaction, a method of exchanging anions using a quaternary ammonium salt-supported polymer cartridge (Chromafix or QMA) is generally used [D. J. Schlyer, M. Bastos, A. P. Wolf, *J. Nucl. Med.* 1987, 28, 764.; S. A. Toorongian, G. K. Mulholland, D. M. Jewett, M. A. Bachelor, M. R. Kilbourn, Nucl. Med. Biol. 1990, 17, 273.; D. M. Jewett, S. A. Toorongian, G. K. Mulholland, G. L. Watkins, M. R. Kilbourn, *Appl. Radiat. Isot.* 1988, 39, 1109.; G. K. Mulholland, R. D. T. J. Mangner, D. M. Jewett, M. R. Kilbourn, *J. Label. Compd. Radiopharm.* 1989, 26, 378.; K. Ohsaki, Y. Endo, S. Yamazaki, M. Tomoi, R. Iwata, *Appl. Radiat. Isot.* 1998, 49, 373-378.].

In order to elute the trapped [$^{18}$F]fluoride from the quaternary ammonium salt-supported polymer cartridge, an aqueous solution containing a metal salt such as K$_2$CO$_3$ or an ammonium salt such as TBAHCO$_3$ is used, and at this time, side reactions such as alcohol or alkene formation occur due to the alkalinity of the salts used during the reaction, which reduces the labeling efficiency. Moreover, complex side products, which are produced during the isolation of the organofluoro-18 compound by HPLC, may cause low specific activity [S. M. Okarvi, *Eur. J. Nucl. Med.* 2001, 28, 929.; J. C. Walsh, K. M. Akhoon, N. Satyamurthy, J. R. Barrio, M. M. Phelps, S. S. Gambhir, T. Toyokuni, *J. Label. Compds. Radiopharm.* 1999, 42, 51.; L. Lang, W. C. Eckelman, *Appl. Radiat. Isot.* 1994, 45, 1155.; L. Lang, W. C. Eckelman, *Appl. Radiat. Isot.* 1997, 48, 169.].

As such, during the elution of the [$^{18}$F]fluoride from the polymer cartridge, the type and concentration of a salt used in the labeling reaction of the [$^{18}$F]fluoride affect the labeling efficiency of the [$^{18}$F]fluoride. Accordingly, there is need to provide a method for eluting the [$^{18}$F]fluoride using a low-concentration of base and preferably for controlling the concentration of the base. Conventionally, a method for producing radiopharmaceuticals by controlling the concentration of the base with the use of inert salts has been reported, but it was found that there was a significant change in the yield of radiopharmaceuticals due to the difference in manufacturers of used inert salts or the difference in manufacturing numbers of the same manufacturer, indicating that it was difficult to ensure a stable supply of radiopharmaceuticals for clinical use. Moreover, in the case of the addition of a small amount of salt directly to a reactor, it was found that there was a change in the concentration of the added salt due to deliquescence of the salt, resulting in a change in the yield [S. Suchiro, S Vallabhajosula, S. J. Goldsmith, D. J. Ballon. *Appl. Radiat. Isot.* 2007, 65, 1350.; B. S. Moon, J. H. Park, H. J. Lee, J. S. Kim, H. S. Kil, B. S. Lee, D. Y. Chi, B. C. Lee, Y. K. Kim, S. E. Kim. *Appl. Radiat. Isot.* 2010, 68, 2279-2284.; S. J. Lee, S. J. Oh, W. Y. Moon, M. S. Choi, J. S. Kim, D. Y. Chi, D. H. Moon, J. S. Ryu. *Nucl. Med. Biol.* 2011, 38, 593.].

Accordingly, the present inventors have made efforts to solve the above-describe problems and found that it was possible to obtain a stable [$^{18}$F]fluoride labeling yield by preventing the concentration of a base from changing due to an inert salt used and it was also possible to stably obtain a [$^{18}$F]fluoride-labeled compound at high purity and high yield by using a [$^{18}$F]fluoride eluent with an adjusted pH to prevent a change in the yield due to a difference in the concentration of the base that was added in a small amount, thereby completing the present invention.

DISCLOSURE

Technical Problem

The present inventors have found that when an eluent containing an inert metal salt or an inert quaternary ammonium salt is used to elute [$^{18}$F]fluoride from an anion exchange polymer support and control the concentration of a base required for labeling with [$^{18}$F]fluoride, the concentration of the base in a reactor is changed, and the degree of the change depends on the manufacturer or manufacturing number of the inert salt added to the eluent. As a result, the [$^{18}$F]fluoride labeling efficiency is changed by the influence of the inert salt contained in the eluent, which makes it difficult to ensure a stable supply for the production of radiopharmaceuticals. Accordingly, an object of the present invention is to provide a stable labeling method at high yield using an eluent that does not affect the concentration of a base in a reactor.

A base is added to a reactor during labeling with [$^{18}$F] fluoride through nucleophilic substitution and, at this time, an error in the concentration of the base in the reactor occurs due to hygroscopicity and deliquescence depending on the type of the base, which affects the labeling efficiency. Accordingly, another object of the present invention is to provide a method for preparing a radiopharmaceutical stably at high yield using an eluent with an adjusted pH without the addition of a base to a reactor.

Technical Solution

To achieve the above objects, the present invention provides a stable [$^{18}$F]fluoride labeling method at high yield, which uses an eluent with an adjusted pH, which is prepared using compounds represented by Formula 1 and Formula 2 as raw materials for inert salts by a method shown in Scheme 1, thereby preventing a change in the concentration of a base required for [$^{18}$F]fluoride labeling reaction.

Moreover, to achieve the above objects, the present invention provides a [$^{18}$F]fluoride labeling method which uses a base as a by-product, which is produced in a process of preparing an eluent with an adjusted pH using potassium carbonate, in [$^{18}$F]fluoride labeling reaction, thus enabling the [$^{18}$F]fluoride labeling reaction only with the eluent with an adjusted pH without the use of an additional base.

[Formula 1]

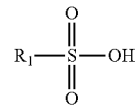

In Formula 1, $R_1$ is a $C_1$-$C_{10}$ primary or secondary alkyl group or aryl group.

MX  [Formula 2]

In Formula 2, M is lithium, sodium, potassium, cesium, rubidium or ammonium, in which the ammonium is a quaternary ammonium represented by the following Formula 3, and X is a hydroxyl ion, a bicarbonate ion, a phosphate ion, a triphosphate ion, or t-butoxide.

[Formula 3]

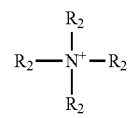

In Formula 3, $R_2$ is hydrogen or a $C_1$-$C_{10}$ primary, secondary or tertiary alkyl group.

[Scheme 1]

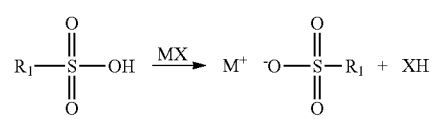

In Scheme 1, $R_1$, M, and X are as defined in Formulas 1 and 2.

Advantageous Effects

According to an aspect of the present invention, the method for labeling with fluorine-18 uses an eluent with an adjusted pH so as to prevent a change in the concentration of a base in a reactor, thereby establishing a stable method for preparing a radiopharmaceutical.

According to another aspect of the present invention, a [$^{18}$F]fluoride labeling method at high yield, which can significantly reduce the generation of by-products without the use of an additional base, is provided to make it possible to prepare a radiopharmaceutical with high specific activity at high yield using a small amount of precursor.

MODE FOR INVENTION

Figure 1:
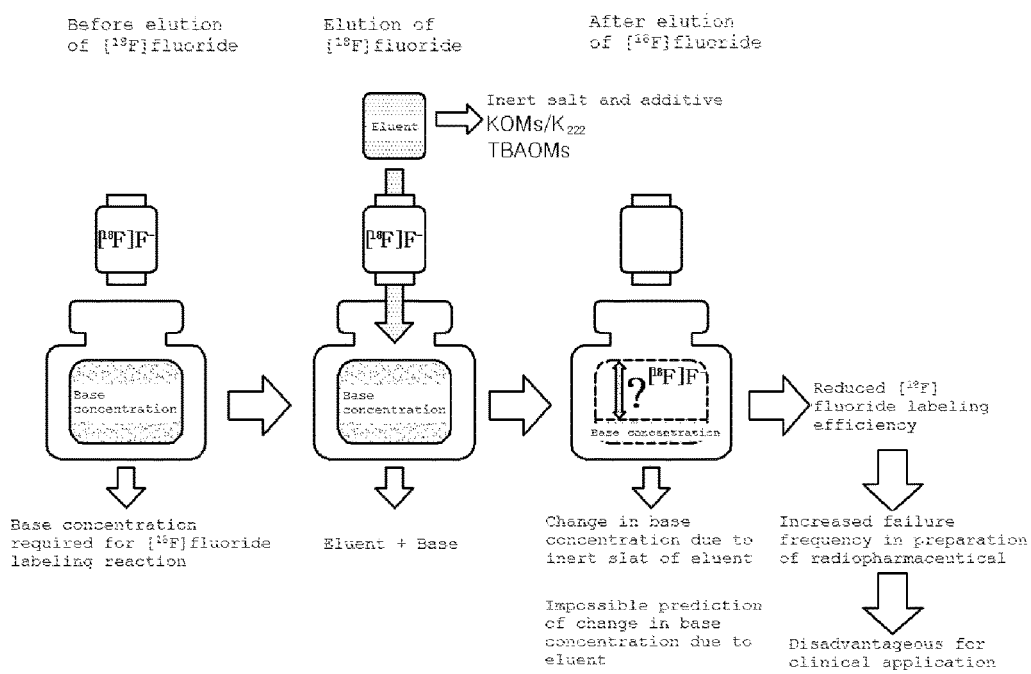
FIG. 1 is a conceptual view showing a [$^{18}$F]fluoride labeling method according to a prior art.

To achieve the above objects, the present invention provides a method for preparing a fluorine-18 eluent with an adjusted pH.

Moreover, whether to use an additional base in a reactor is determined based on the concentration of the eluent prepared by the above method and, at this time, the present invention provides a method for labeling with fluorine-18 by reacting the eluted [$^{18}$F]fluoride with an alkyl halide or alkyl sulfonate in the presence of a reaction solvent.

Hereinafter, the present invention will be described in detail.

The first step is to prepare a fluorine-18 eluent with an adjusted pH.

In the method for preparing an eluent according to the present invention, in the sulfonic acid represented by Formula 1, $R_1$ is an alkyl group or aryl group. More specifically, the alkyl group is preferably a $C_1$-$C_{18}$ alkyl sulfonic acid or halo $C_1$-$C_{10}$ alkyl group, and examples thereof include methanesulfonic acid, ethanesulfonic acid, isopropanesulfonic acid, chloromethanesulfonic acid, trifluoromethanesulfonic acid, and chloroethanesulfonic acid. Moreover, the aryl group is preferably selected from the group consisting of a phenyl group, a $C_1$-$C_4$ alkyl phenyl group, a halo phenyl group, a $C_1$-$C_4$ alkoxy phenyl group, and a nitrophenyl group, and preferred examples thereof include methylphenylsulfonic acid, ethylphenylsulfonic acid, chlorophenylsulfonic acid, bromophenylsulfonic acid, methoxyphenylsulfonic acid, and nitrophenylsulfonic acid.

In the method for preparing an eluent according to the present invention, in the base represented by Formula 2, M is a metal or quaternary ammonium, preferably lithium, sodium, potassium, cesium, rubidium or ammonium, and X is a base, preferably a hydroxyl ion, a carbonate ion, a bicarbonate ion, a phosphate ion, a diphosphate ion, a triphosphate ion, or t-butoxide, more preferably potassium hydroxide (KOH) or tetrabutylammonium hydroxide (TBAOH), which is mixed with the compound of Formula 1 to prepare an eluent having a pH of 6.0 to 8.0. When the pH of the eluent is less than 6.0, the amount of a base additionally required is increased, and when the pH exceeds 8.0, the precursor is decomposed by the eluent itself, which is problematic in the [$^{18}$F]fluoride labeling efficiency.

In the method for preparing an eluent according to the present invention, the solvent used for the elution is acetonitrile or alcohol containing water, and the alcohol may be selected from the group consisting of a primary alcohol such as methanol, ethanol, n-propanol, n-butanol, amyl alcohol, n-hexyl alcohol, n-heptanol, n-octanol, etc.; a secondary alcohol such as isopropanol, isobutanol, isoamyl alcohol, 3-pentanol, etc.; and a tertiary alcohol such as t-butanol, t-amyl alcohol, 2,3-dimethyl-2-butanol, 2-(trifluoromethyl)-2-propanol, 3-methyl-3-pentanol, 3-ethyl-3-pentanol, 2-methyl-2-pentanol, 2,3-dimethyl-3-pentanol, 2,4-dimethyl-2-pentanol, 2-methyl-2-hexanol, 2-cyclopropyl-2-propanol, 2-cyclopropyl-2-butanol, 2-cyclopropyl-3-methyl-2-butanol, 1-methylcyclopentanol, 1-ethylcyclopentanol, 1-propylcyclopentanol, 1-methylcyclohexanol, 1-ethylcyclohexanol, 1-methylcycloheptanol, etc., but may preferably be selected from primary alcohols such as methanol and ethanol.

In the method for labeling with fluorine-18 according to the present invention, the eluent prepared by the above method is used to elute [$^{18}$F]fluoride trapped in an anion exchange polymer support to a reactor, and a base required for [$^{18}$F]fluoride labeling reaction is added dropwise to the reactor. Referring to the following Tables 1 and 2, it can be seen that the use of a conventional eluent affects the concentration of the base in the reactor, which changes the [$^{18}$F]fluoride labeling efficiency; however, the use of the eluent prepared by the above method enables stable labeling with [$^{18}$F]fluoride at high yield.

Here, the base added to the reactor is the base of Formula 2 and may preferably be selected from the group consisting of potassium carbonate ($K_2CO_3$), potassium hydrogen carbonate ($KHCO_3$), potassium hydroxide (KOH), tetrabutylammonium hydrogen carbonate ($TBAHCO_3$), and tetrabutylammonium hydroxide (TBAOH).

When the pH of the eluent is in the range of 7.0 to 8.0, the [$^{18}$F]fluoride labeling reaction is possible even without the addition of a base to the reaction, and it can be seen from the following Table 3 that the labeling efficiency varies depending on the pH of the eluent, and even when the amount of the precursor is reduced, a high labeling efficiency is maintained at an optimal pH.

In the method for labeling with organofluorine-18, the reaction solvent is an aprotic solvent or protic solvent. The aprotic solvent may preferably be acetonitrile, dimethylformamide, and dimethylsulfoxide, and the protic solvent may preferably be alcohol, more preferably a tertiary alcohol selected from the group consisting of t-butanol, t-amyl alcohol, 2,3-dimethyl-2-butanol, 2-(trifluoromethyl)-2-propanol, 3-methyl-3-pentanol, 3-ethyl-3-pentanol, 2-methyl-2-pentanol, 2,3-dimethyl-3-pentanol, 2,4-dimethyl-2-pentanol, 2-methyl-2-hexanol, 2-cyclopropyl-2-propanol, 2-cyclopropyl-2-butanol, 2-cyclopropyl-3-methyl-2-butanol, 1-methylcyclopentanol, 1-ethylcyclopentanol, 1-propylcyclopentanol, 1-methylcyclohexanol, 1-ethylcyclohexanol, and 1-methylcycloheptanol, and most preferably a tertiary alcohol selected from the group consisting of t-butanol, t-amyl alcohol, and 2,3-dimethyl-2-butanol.

In a method for preparing an organofluoro-18 compound according to the present invention, the organofluoro-18 compound prepared by the above method may be [$^{18}$F] fluoropropyl-carbomethoxytropane represented by the following Formula 5:

[Formula 5]

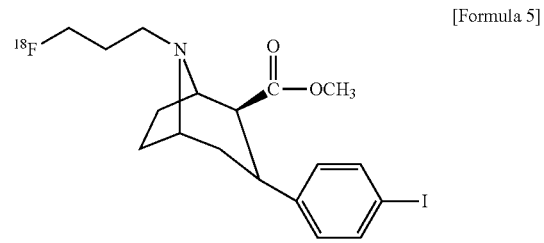

In the method for preparing an organofluoro-18 compound according to the present invention, the organofluoro-18 compound prepared by the above method may be [$^{18}$F] fluoromisonidazole represented by the following Formula 8:

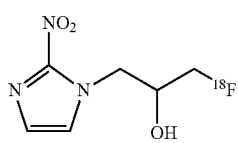

[Formula 8]

In the method for preparing an organofluoro-18 compound according to the present invention, the organofluoro-18 compound prepared by the above method may be [$^{18}$F]fluorothymidine represented by the following Formula 11:

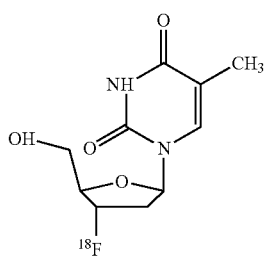

[Formula 11]

In the method for preparing an organofluoro-18 compound according to the present invention, the organofluoro-18 compound prepared by the above method may be [$^{18}$F]fluoroestradiol represented by the following Formula 12:

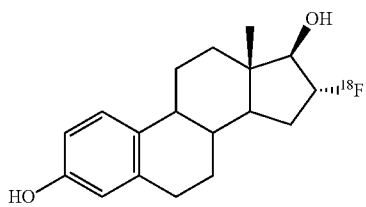

[Formula 12]

In the method for preparing an organofluoro-18 compound according to the present invention, the organofluoro-18 compound prepared by the above method may be [$^{18}$F]fluorodeoxyglucose represented by the following Formula 13:

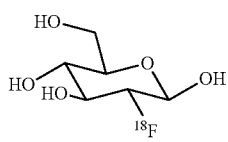

[Formula 13]

In the method for preparing an organofluoro-18 compound according to the present invention, the organofluoro-18 compound prepared by the above method may be [$^{18}$F]fluoroDDNP represented by the following Formula 14:

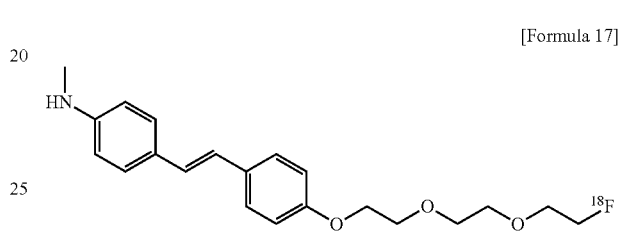

[Formula 14]

In the method for preparing an organofluoro-18 compound according to the present invention, the organofluoro-18 compound prepared by the above method may be [$^{18}$F]fluorobetaben represented by the following Formula 17:

[Formula 17]

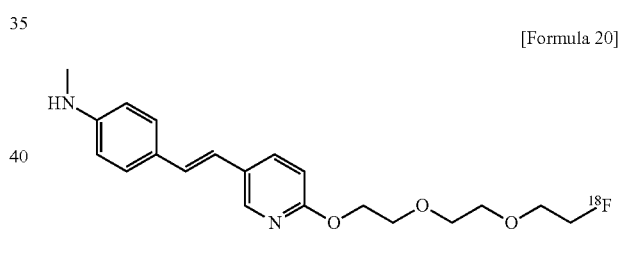

In the method for preparing an organofluoro-18 compound according to the present invention, the organofluoro-18 compound prepared by the above method may be [$^{18}$F]fluorobetapir represented by the following Formula 20:

[Formula 20]

In the method for preparing an organofluoro-18 compound according to the present invention, the organofluoro-18 compound prepared by the above method may be [$^{18}$F]FHBG represented by the following Formula 21:

[Formula 21]

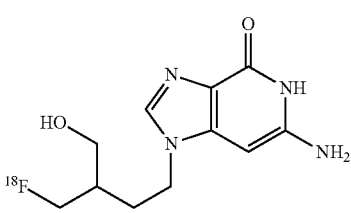

In the method for preparing an organofluoro-18 compound according to the present invention, the organofluoro-18 compound prepared by the above method may be [$^{18}$F]HX4 represented by the following Formula 22:

[Formula 22]

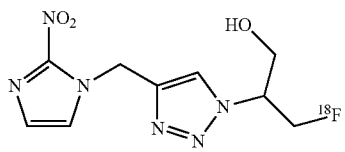

Next, the present invention will be described in more detail with reference to FIG. 1.

FIG. 1 is a conceptual view showing a [$^{18}$F]fluoride labeling method according to a prior art;

Specifically, [$^{18}$F]fluoride trapped in an anion exchange polymer support is eluted into a reactor using an eluent containing an inert salt. The reactor contains a base required for [$^{18}$F]fluoride labeling reaction. At this time, the concentration of the base present in the reactor may be changed by the eluent. As a result, the base required for the [$^{18}$F]fluoride labeling reaction may be lost, which reduces the [$^{18}$F] fluoride labeling efficiency and makes it difficult to predict the change in the concentration of the base present in the reactor, which is more problematic.

Figure 2:
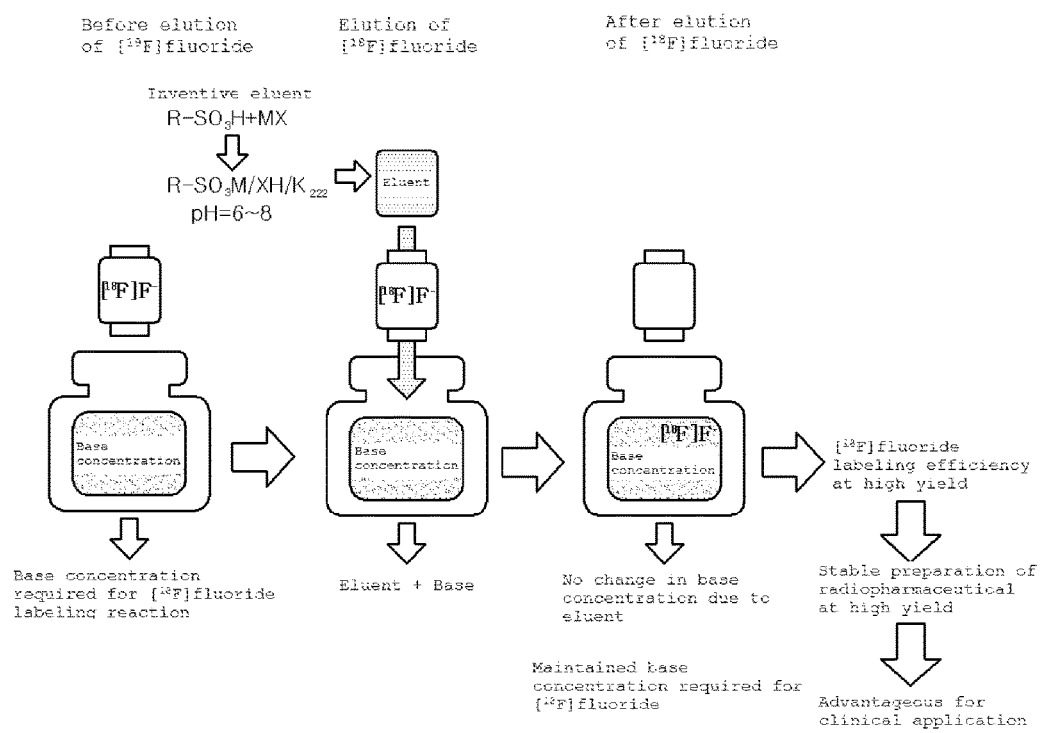
FIG. 2 is a conceptual view showing a [$^{18}$F]fluoride labeling method in accordance with an embodiment of the present invention.

FIG. 2 is a conceptual view showing a [$^{18}$F]fluoride labeling method in accordance with an embodiment of the present invention.

Specifically, [$^{18}$F]fluoride trapped in an anion exchange polymer support is eluted into a reactor using an eluent with an adjusted pH of 6.0 to 8.0, prepared using the sulfonic acid of Formula 1 and the base of Formula 2. At this time, the reactor contains a base required for [$^{18}$F]fluoride labeling reaction. According to the above method, the concentration of the base present in the reactor is not changed by the eluent used for the elution, and thus the [$^{18}$F]fluoride labeling efficiency at high yield can be maintained stable.

Figure 3:
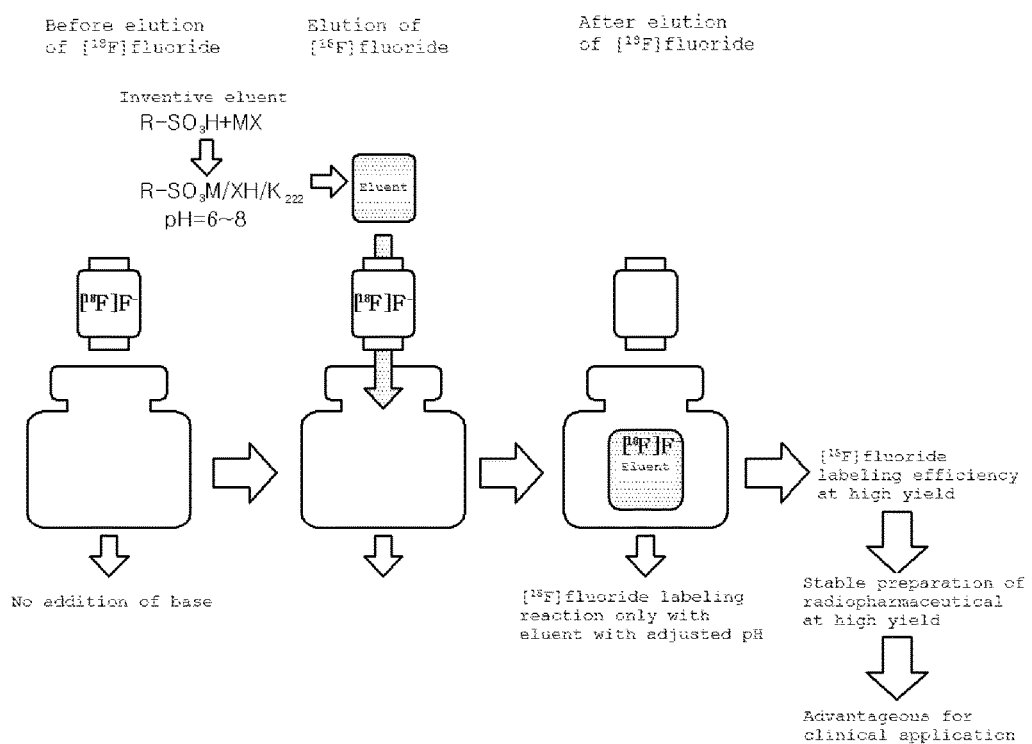
FIG. 3 is a conceptual view showing a [$^{18}$F]fluoride labeling method in accordance with another embodiment of present invention.

FIG. 3 is a conceptual view showing a [$^{18}$F]fluoride labeling method in accordance with another embodiment of present invention.

Specifically, [$^{18}$F]fluoride trapped in an anion exchange polymer support is eluted into a reactor using an eluent with adjusted pHs of 7.0 to 8.0, prepared using the sulfonic acid of Formula 1 and the base of Formula 2. At this time, the reactor contains no base required for [$^{18}$F]fluoride labeling reaction in the reactor. According to the above method, the [$^{18}$F]fluoride labeling reaction is performed using only the eluent used for the elution, which makes it possible to prevent a variation in the labeling efficiency caused by an error in the concentration of the base, which occurs upon further addition of the base, and thus the [$^{18}$F]fluoride labeling efficiency at high yield can be maintained stable.

In this aspect, the present invention can be effectively applied to the preparation of a radiopharmaceutical labeled with [$^{18}$F]fluoride, a radioisotope, and in particular can be easily applied to any type of automated synthesis apparatus. The present invention has applications to the synthesis of radiopharmaceuticals labeled with [F]fluoride, a radioisotope.

BEST MODE FOR CARRYING OUT INVENTION

Next, the present invention will be described in more detail with reference to the following Examples. However, these examples are merely illustrative of the preset invention, and the scope of the present invention is not limited by these examples. It will be appreciated by those skilled in the art that various modifications and changes can be made without departing from the scope of the present invention, and all such modifications and changes are intended to be included within the scope of the present invention.

Example 1

Preparation 1 of Organofluoro-18 Compound

Synthesis of [$^{18}$F]fluoropropyl-carbomethoxytropane

The synthesis process of [$^{18}$F]fluoropropyl-carbomethoxytropane is shown in Scheme 2. [$^{18}$F]fluoride was passed through a quaternary ammonium support (Chromafix or QMA) to be adsorbed thereon by exchanging anions, and the [$^{18}$F]fluoride adsorbed on the quaternary ammonium support was eluted into a reactor containing a base (TBAOH: 2 mg) using an eluent with an adjusted pH, prepared using methanesulfonic acid and potassium hydroxide, and 100 µL of acetonitrile solution containing Kryptofix (K222). After the elution, the eluent was completely removed by azeotropic distillation while introducing nitrogen gas at 100° C. 0.1 mL of acetonitrile, in which 4 mg of N-(3-methanesulfonyloxypropyl)-2µ-carbomethoxy-3-β-(4-iodophenyl)tropane or N-(3-toluenesulfonyloxypropyl)-2β-carbomethoxy-3-β-(4-iodophenyl)tropane was dissolved, and 1.0 mL of t-amyl alcohol were placed in the reactor and reacted at 120° C. for 20 minutes to synthesize compound 5, and the labeling efficiency was analyzed by a radio thin-layer chromatography.

[Scheme 2]

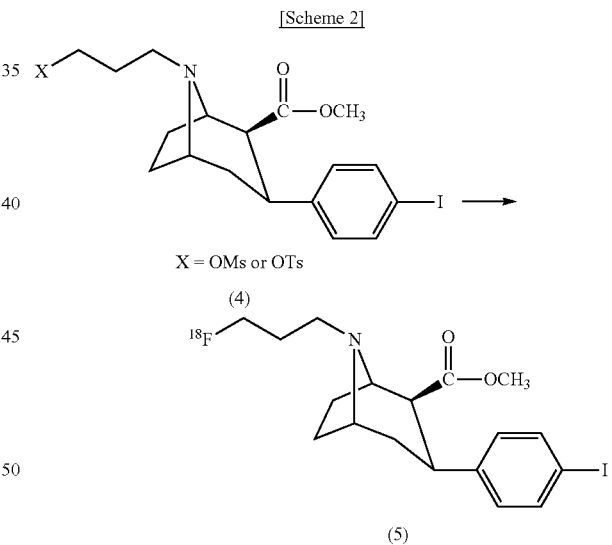

Comparative Examples 1-8

Preparation 2 of Organofluoro-18 Compound

Synthesis of [$^{18}$F]fluoropropyl-carbomethoxytropane

In order to examine the effect of a conventional eluent using an inert metal salt on the labeling efficiency, the labeling efficiency was measured using inert metal salts having different manufacturing numbers and prepared by the same manufacturer.

Compound 5 was synthesized by the same method as in Example 1, except that [$^{18}$F]fluoride adsorbed on the quaternary ammonium support (Chromafix or QMA) was eluted with a conventionally used eluent, i.e., an eluent using an inert metal salt KOMs, and various concentrations of base (TBAOH 2 to 8 mg) were used for [$^{18}$F]fluoride labeling reaction.

TABLE 1

| Examples | Manu-facturing number of KOMs | Manu-facturing number of eluent | Eluent pH | Amount of base in reactor (mg) | TLC yield (%) |
|---|---|---|---|---|---|
| Example 1 | Inventive eluent | — | 7.00 | 2 | 74.19 ± 4.2 |
| Comparative Example 1 | BCBC4256 | KOMs-1 | 7.01 | 2 | 0 |
| Comparative Example 2 | BCBC4256 | KOMs-1 | 7.01 | 4 | 47.13 |
| Comparative Example 3 | BCBC4256 | KOMs-2 | 5.97 | 5 | 0 |
| Comparative Example 4 | BCBC4256 | KOMs-2 | 5.97 | 7 | 55.35 |
| Comparative Example 5 | BCBC4256 | KOMs-3 | 5.21 | 7 | 65.58 |
| Comparative Example 6 | BCBC4256V | KOMs-4 | 6.57 | 5 | 20.67 |
| Comparative Example 7 | BCBC4256V | KOMs-4 | 6.57 | 6 | 37.22 |
| Comparative Example 8 | BCBC4256V | KOMs-4 | 6.57 | 8 | 73.40 |

As shown in Table 1, it was found that the inventive eluent showed a stable yield of 74.19±4.2% with the use of 2 mg base, while in the case of Comparative Examples 1-5, even the use of KOMs having the same manufacturing number showed various pHs during the preparation, resulting in a significant change in TLC yield. Even the use of KOMs having different manufacturing numbers resulted in a difference in yield of more than 20% at the same base concentration (Comparative Examples 3 and 6).

Experimental Example 1

Preparation 3 of Organofluoro-18 Compound

Synthesis of [$^{18}$F]fluoropropyl-carbomethoxytropane

In order to examine whether the concentration of the base present in the reactor was affected by the use of the conventional inert metal salt KOMs, compound 5 was synthesized by the same method as in Example 1, except that [$^{18}$O]H$_2$O solution containing [$^{18}$O]fluoride was placed in a reactor containing a base (TBAOH: 2 mg) without the use of a quaternary ammonium support (Chromafix or QMA), and then the eluent was completely removed by azeotropic distillation while introducing nitrogen gas at 100° C.

Experimental Examples 2-5

Preparation 4 of Organofluoro-18 Compound

Synthesis of [$^{18}$F]fluoropropyl-carbomethoxytropane

Compound 5 was synthesized by the same method as in Example 1, except that insert metal salts KOMs and various concentrations of base (TBAOH 2 to 5 mg) were previously placed in the reactor.

TABLE 2

| Examples | 0.2M KOMs solution (μL) | Amount of base in reactor (mg) | TLC yield (%) |
|---|---|---|---|
| Expeimental Example 1 | — | 2 | 37.62 |
| Expeimental Example 2 | 100 | 2 | 0 |
| Expeimental Example 3 | 100 | 3 | 1.16 |
| Expeimental Example 4 | 100 | 4 | 47.13 |
| Expeimental Example 5 | 100 | 5 | 17.29 |

As shown in Table 2, it was found that the addition of the KOMs solution resulted in a decrease in the TLC yield from 37.62% to 0% even during the reaction using the same base and the increased amount of base from 2 mg to 4 mg results in a TLC yield of 47.13%. Therefore, it was indirectly confirmed that about 2 mg of salt required for the reaction was lost by KOMs.

Example 2

Preparation 5 of Organofluoro-18 Compound

Synthesis of [$^{18}$F]fluoropropyl-carbomethoxytropane

Compound 5 was synthesized by the same method as in Example 1, except that [$^{18}$F]fluoride adsorbed on the quaternary ammonium support (Chromafix or QMA) was eluted using eluents with various pHs of 7.0 to 7.8, prepared using methanesulfonic acid and various bases, without the addition of a base to the reactor.

TABLE 3

| Eluents | Types of bases used for preparation of eluent | Eluent pH | TLC yield (%) |
|---|---|---|---|
| 1 | KOH | 7.2 | 12.31 |
| 2 | KOH | 7.4 | 6.37 |
| 3 | t-BuOK | 7.2 | 9.22 |
| 4 | t-BuOK | 7.4 | 4.35 |
| 5 | K2CO3 | 7.2 | 60.15 |
| 6 | K2CO3 | 7.4 | 70.55 |

As shown in Table 3, it was found that the use of various types of bases for the preparation of the eluents at the same pH resulted in a difference in the TLC yield of up to 66% and the use of K$_2$CO$_3$ resulted in a labeling efficiency of up to 70.55%. Therefore, it can be seen that the [$^{18}$F]fluoride labeling reaction can be stably performed by adjusting the pH of the eluent without the addition of a small amount of base to the rector.

Example 3

Preparation 6 of Organofluoro-18 Compound

Synthesis of [$^{18}$F]fluoromisonidazole

The synthesis process of [$^{18}$F]fluoromisonidazole is shown in Scheme 3. [$^{18}$F]fluoride was labeled by the same method as in Example 1, except that [$^{18}$F]fluoride was eluted from a quaternary ammonium support using eluents with various pHs of 7.0 to 7.8, prepared using methanesulfonic acid and potassium carbonate (KHCO$_3$), and 1 to 5 mg of 3-(2-nitroimidazol-1-yl)-2-O-tetrahydropyranyl-1-O-toluenesulfonyl propanediol was dissolved in 1 mL of acetonitrile and reacted at 100° C. The [$^{18}$F]fluoride labeling efficiency was analyzed by a radio thin-layer chromatography scanner (radio TLC scanner), and then compound 8 was synthesized by adding 0.5 mL of 1 M hydrochloric acid, followed by hydrolysis at 100° C. for 5 minutes. Subsequently, 250 mL of 2 M sodium hydroxide was added for neutralization, and then 250 mL of citrate buffer was added, and purified by HPLC.

[Scheme 3]

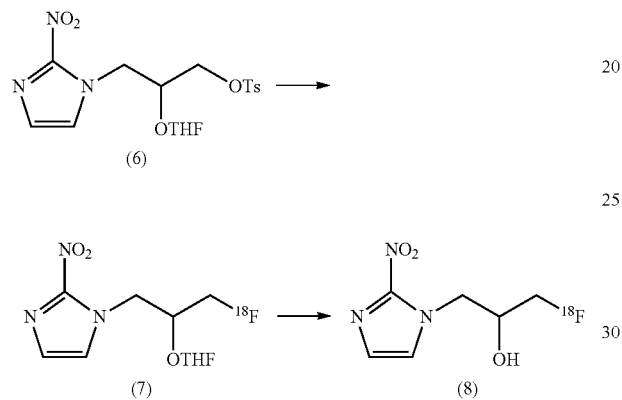

(6)

(7)

(8)

TABLE 4

| Eluents | Amount of precursor (mg) | Eluent pH | TLC yield (%) |
|---|---|---|---|
| 1 | 5 | 7.4 | 98.76 |
| 2 | 1 | 7.4 | 68.30 |
| 3 | 1 | 7.6 | 93.60 |
| 4 | 1 | 7.8 | 92.41 |

Example 4

Preparation 7 of Organofluoro-18 Compound

Synthesis of [$^{18}$F]fluorothymidine

The synthesis process of [$^{18}$F]fluorothymidine is shown in Scheme 4. [$^{18}$F]fluoride was labeled by the same method as in Example 1, except that [$^{18}$F]fluoride was eluted from a quaternary ammonium support using an eluent with a pH of 7.4, prepared using methanesulfonic acid and potassium carbonate (KHCO$_3$), and 5 mg of (5'-O-DMTr-2'-deoxy-3'-O-nosyl-β-D-threo-pentofuranosyl)-3-N-BOC-thymine was dissolved in 1 mL of acetonitrile and reacted at 100° C. The [$^{18}$F]fluoride labeling efficiency was analyzed by a radio thin-layer chromatography scanner (radio TLC scanner), and the labeling efficiency was measured to be 75.67%. After the labeling reaction, compound 11 was synthesized by adding 0.5 mL of 1 M hydrochloric acid, followed by hydrolysis at 100° C. for 5 minutes. Subsequently, 250 mL of 2 M sodium hydroxide was added for neutralization, and then 250 mL of citrate buffer was added, and purified by HPLC.

[Scheme 4]

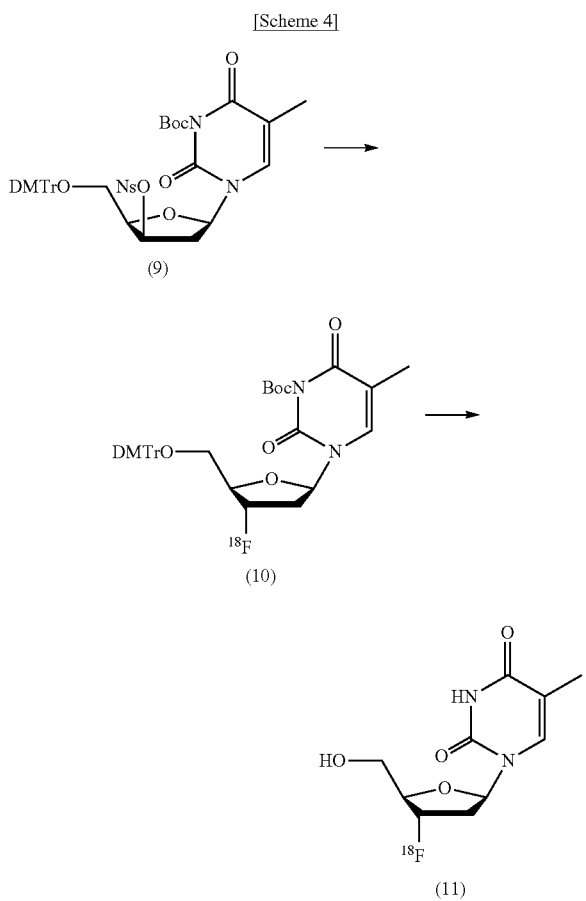

(9)

(10)

(11)

Example 5

Preparation 8 of Organofluoro-18 Compound

Synthesis of [$^{18}$F]fluorobetaben

The synthesis process of [$^{18}$F]fluorobetaben is shown in Scheme 5. [$^{18}$F]fluoride was labeled by the same method as in Example 1, except that [$^{18}$F]fluoride was eluted from a quaternary ammonium support using an eluent with a pH of 7.4, prepared using methanesulfonic acid and potassium carbonate (KHCO$_3$), and 4 mg of (E)-2-(2-(2-(4-(4-(tert-butoxycarbonyl(methyl)amino)styryl)phenoxy)ethoxy)ethoxy)ethyl methanesulfonate was dissolved in 1 mL of acetonitrile and reacted at 120° C. The [$^{18}$F]fluoride labeling efficiency was analyzed by a radio thin-layer chromatography scanner (radio TLC scanner), and the labeling efficiency was measured to be 75.67%. After the labeling reaction, compound 17 was synthesized by adding 0.5 mL of 1 M hydrochloric acid, followed by hydrolysis at 100° C. for 5 minutes. Subsequently, 250 mL of 2 M sodium hydroxide was added for neutralization and then purified by HPLC.

[Scheme 5]

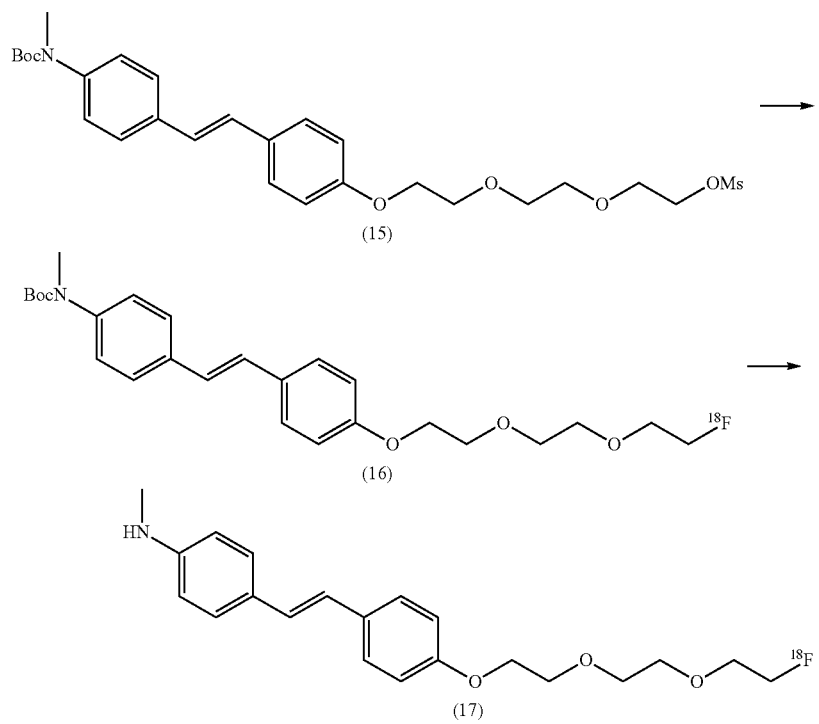

Example 6

Preparation 9 of Organofluoro-18 Compound

Synthesis of [$^{18}$F]fluorobetapir

The synthesis process of [$^{18}$F]fluorobetapir is shown in Scheme 6. Compound 20 was synthesized by the same method as in Example 1, except that [$^{18}$F]fluoride was eluted from a quaternary ammonium support using an eluent with a pH of 7.4, prepared using methanesulfonic acid and potassium carbonate (KHCO$_3$), and 4 mg of (E)-2-(2-(2-(5-(4-(tert-butoxycarbonyl(methyl)amino)styryl)pyridin-2-yloxy)ethoxy)ethoxy)ethyl methanesulfonate was dissolved in 1 mL of acetonitrile and reacted at 120° C. The [$^{18}$F] fluoride labeling efficiency was analyzed by a radio thin-layer chromatography scanner (radio TLC scanner), and the labeling efficiency was measured to be 80.38%.

[Scheme 6]

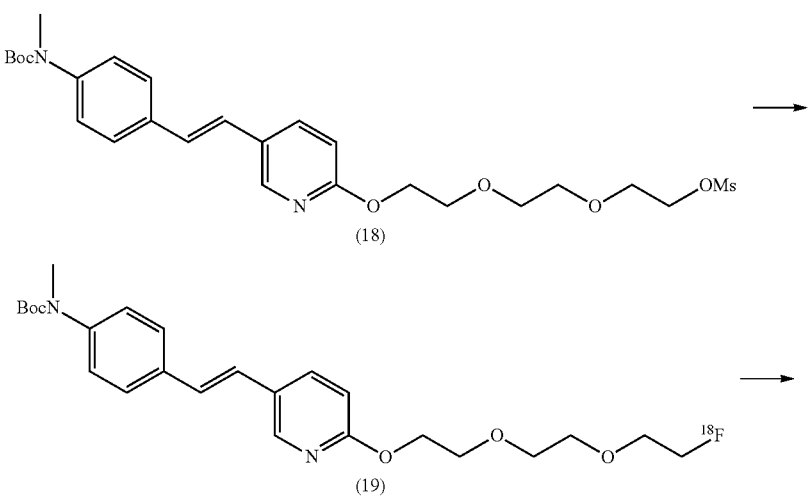

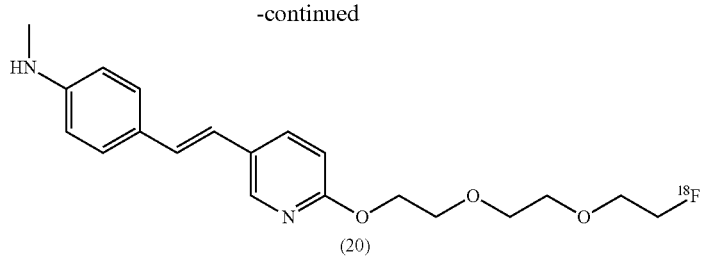

(20)

The invention claimed is:

1. A method for preparing an organic [$^{18}$F]fluoro compound, the method comprising the steps of:
   (a) preparing an eluent by a method comprising reacting compounds represented by Formula 1 and Formula 2 as shown in Scheme 1:

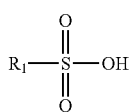

[Formula 1]

wherein $R_1$ is a $C_1$-$C_{10}$ primary or secondary alkyl group or aryl group;

MX          [Formula 2]

wherein M is lithium, sodium, potassium, cesium, or rubidium, and X is a hydroxyl ion, a carbonate ion, a bicarbonate ion, a phosphate ion, a diphosphate ion, a triphosphate ion, or t-butoxide;

[Scheme 1]

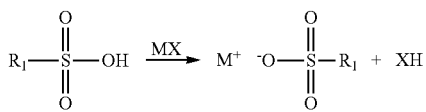

wherein $R_1$, M, and X are as defined in Formulas 1 and 2, and wherein the pH of the eluent is adjusted to 6.0 to 8.0;
   (b) eluting an [$^{18}$F]fluoride adsorbed on a quaternary ammonium support into a reactor using the eluent;
   (c) removing the eluent in the reactor after the elution; and
   (d) reacting an alkyl halide or alkyl sulfonate with the eluted [$^{18}$F]fluoride in the presence of a reaction solvent,
   wherein the alkyl halide or alkyl sulfonate is selected from the group consisting of N-(3-methanesulfonyloxypropyl)-2β-carbomethoxy-3-β-(4-iodophenyl) tropane, N-(3-toluenesulfonyloxypropyl)-2β-carbomethoxy-3-β-(4-iodophenyl)tropane, 3-(2-nitroimidazol-1-yl)-2-O-tetrahydropyranyl-1-O-toluenesulfonyl propanediol, (5'-O-DMTr-2'-deoxy-3'-O-nosyl-β-D-threo-pentofuranosyl)-3-N-BOC-thymine, (E)-2-(2-(2-(4-(4-(tert-butoxycarbonyl (methyl)amino)styryl)phenoxy)ethoxy)ethyl methanesulfonate and (E)-2-(2-(2-(5-(4-(tert-butoxycarbonyl(methyl)amino)styryl)pyridin-2-yloxy) ethoxy)ethyl methanesulfonate.

2. The method of claim 1, wherein the reactor solvent is an aprotic solvent or protic solvent.

3. The method of claim 2, wherein the aprotic solvent is any one selected from the group consisting of acetonitrile, dimethylformamide, and dimethylsulfoxide.

4. The method of claim 2, wherein the protic solvent is a primary alcohol selected from the group consisting of methanol, ethanol, n-propanol, n-butanol, n-amyl alcohol, n-hexyl alcohol, n-heptanol, and n-octanol; a secondary alcohol selected from the group consisting of isopropanol, isobutanol, isoamyl alcohol, and 3-pentanol; and a tertiary alcohol selected from the group consisting of t-butanol, t-amyl alcohol, 2,3-dimethyl-2-butanol, 2-(trifluoromethyl)-2-propanol, 3-methyl-3-pentanol, 3-ethyl-3-pentanol, 2-methyl-2-pentanol, 2,3-dimethyl-3-pentanol, 2,4-dimethyl-2-pentanol, 2-methyl-2-hexanol, 2-cyclopropyl-2-propanol, 2-cyclopropyl-2-butanol, 2-cyclopropyl-3-methyl-2-butanol, 1-methylcyclopentanol, 1-ethylcyclopentanol, 1-propylcyclopentanol, 1-methylcyclohexanol, 1-ethylcyclohexanol, and 1-methylcycloheptanol.

5. A method for preparing an organic [$^{18}$F]fluoro compound, the method comprising the steps of:
   (a) preparing an eluent by a method comprising reacting compounds represented by Formula 1 and Formula 2 as shown in Scheme 1:

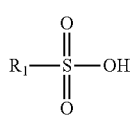

[Formula 1]

wherein $R_1$ is a $C_1$-$C_{10}$ primary or secondary alkyl group or aryl group;

MX          [Formula 2]

wherein M is lithium, sodium, potassium, cesium, or rubidium, and X is a hydroxyl ion, a carbonate ion, a bicarbonate ion, a phosphate ion, a diphosphate ion, a triphosphate ion, or t-butoxide;

[Scheme 1]

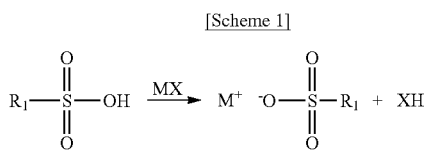

wherein $R_1$, M, and X are as defined in Formulas 1 and 2, and wherein the pH of the eluent is adjusted to 6.0 to 8.0;

(b) eluting an [$^{18}$F]fluoride adsorbed on a quaternary ammonium support into a reactor using the eluent; and (c) reacting an alkyl halide or alkyl sulfonate with the eluted [$^{18}$F]fluoride in the presence of the eluent in the reactor after the elution as a reaction solvent, wherein the alkyl halide or alkyl sulfonate is selected from the group consisting of N-(3-methanesulfonyloxypropyl)-2β-carbomethoxy-3-β-(4-iodophenyl)tropane, N-(3-toluenesulfonyloxypropyl)-2β-carbomethoxy-3-β-(4-iodophenyl)tropane, N-3-(2-nitroimidazol-1-yl)-2-O-tetrahydropyranyl-1-O-toluenesulfonyl propanediol, (5'-O-DMTr-2'-deoxy-3'-O-nosyl-β-D-threo-pentofuranosyl)-3-N-BOC-thymine, (E)-2-(2-(2-(4-(4-(tert-butoxycarbonyl(methyl)amino)styryl)phenoxy)ethoxy)ethoxy)ethyl methanesulfonate and (E)-2-(2-(2-(5-(4-(tert-butoxycarbonyl(methyl)amino)styryl)pyridin-2-yloxy)ethoxy)ethoxy)ethyl methanesulfonate.

* * * * *